(12) United States Patent
Chatelier et al.

(10) Patent No.: US 10,151,724 B2
(45) Date of Patent: Dec. 11, 2018

(54) SYSTEMS AND METHODS OF DISCRIMINATING BETWEEN A CONTROL SAMPLE AND A TEST FLUID USING CAPACITANCE

(71) Applicant: Cilag GmbH International, Zug (CH)

(72) Inventors: Ronald C. Chatelier, Bayswater (AU); Alastair M. Hodges, Blackburn South (AU)

(73) Assignee: LIFESCAN IP HOLDINGS, LLC, Wayne, PA (US)

( * ) Notice: Subject to any disclaimer, the term of this patent is extended or adjusted under 35 U.S.C. 154(b) by 631 days.

(21) Appl. No.: 14/087,473

(22) Filed: Nov. 22, 2013

(65) Prior Publication Data

US 2014/0151244 A1 Jun. 5, 2014

Related U.S. Application Data

(62) Division of application No. 12/895,067, filed on Sep. 30, 2010, now Pat. No. 8,617,370.

(51) Int. Cl.
*G01N 27/28* (2006.01)
*C12Q 1/00* (2006.01)
(Continued)

(52) U.S. Cl.
CPC ............ *G01N 27/28* (2013.01); *C12Q 1/005* (2013.01); *G01N 27/3274* (2013.01); *G01N 33/48707* (2013.01)

(58) Field of Classification Search
None
See application file for complete search history.

(56) References Cited

U.S. PATENT DOCUMENTS 5,385,846 A 1/1995 Kuhn et al.
5,620,579 A 4/1997 Genshaw et al.
(Continued)

FOREIGN PATENT DOCUMENTS

EP 0735363 A1 10/1996
EP 1 156 324 A1 11/2001
(Continued)

OTHER PUBLICATIONS

Japanese Office Action for JP 2013-530812; dated Jun. 2, 2015; 3 pages.

(Continued)

*Primary Examiner* — Gurpreet Kaur
*Assistant Examiner* — Steven E Rosenwald
(74) *Attorney, Agent, or Firm* — Barclay Damon, LLP

(57) ABSTRACT

Methods for distinguishing between an aqueous non-blood sample (e.g., a control solution) and a blood sample are provided herein. In one aspect, the method includes using a test strip in which multiple current transients are measured by a meter electrically connected to an electrochemical test strip. The current transients are used to determine if a sample is a blood sample or an aqueous non-blood sample based on characteristics of the sample (e.g., amount of interferent present, reaction kinetics, and/or capacitance). The method can also include calculating a discrimination criteria based upon these characteristics. Various aspects of a system for distinguishing between a blood sample and an aqueous non-blood sample are also provided herein.

5 Claims, 8 Drawing Sheets

(51) Int. Cl.
*G01N 27/327* (2006.01)
*G01N 33/487* (2006.01)

(56) References Cited

U.S. PATENT DOCUMENTS

| | | | |
|---|---|---|---|
| 5,653,863 A | 8/1997 | Genshaw et al. | |
| 5,781,455 A | 7/1998 | Hyodo | |
| 5,858,648 A | 1/1999 | Steel et al. | |
| 5,942,102 A | 8/1999 | Hodges et al. | |
| 6,174,420 B1 | 1/2001 | Hodges et al. | |
| 6,193,873 B1 | 2/2001 | Ohara et al. | |
| 6,241,862 B1 | 6/2001 | McAleer et al. | |
| 6,284,125 B1 | 9/2001 | Hodges et al. | |
| 6,379,513 B1 | 4/2002 | Chambers et al. | |
| 6,413,410 B1 | 7/2002 | Hodges et al. | |
| 6,424,847 B1 | 7/2002 | Mastrototaro et al. | |
| 6,475,360 B1 | 11/2002 | Hodges et al. | |
| 6,475,372 B1 | 11/2002 | Ohara et al. | |
| 6,521,110 B1 | 2/2003 | Hodges et al. | |
| 6,576,117 B1 | 6/2003 | Iketaki et al. | |
| 6,599,407 B2 | 7/2003 | Taniike et al. | |
| 6,632,349 B1 | 10/2003 | Hodges et al. | |
| 6,638,415 B1 | 10/2003 | Hodges et al. | |
| 6,676,995 B2 | 1/2004 | Dick et al. | |
| 6,749,887 B1 | 6/2004 | Dick et al. | |
| 6,780,645 B2 | 8/2004 | Hayter et al. | |
| 6,797,150 B2 | 9/2004 | Kermani et al. | |
| 6,830,934 B1 | 12/2004 | Harding et al. | |
| 6,856,125 B2 | 2/2005 | Kermani | |
| 6,869,411 B2 | 3/2005 | Langley et al. | |
| 6,872,298 B2 | 3/2005 | Kermani | |
| 6,895,263 B2 | 5/2005 | Shin et al. | |
| 6,946,067 B2 | 9/2005 | Hodges et al. | |
| 7,043,821 B2 | 5/2006 | Hodges | |
| 7,045,054 B1 | 5/2006 | Buck et al. | |
| 7,195,704 B2 | 3/2007 | Kermani et al. | |
| 7,199,594 B2 | 4/2007 | Kermani | |
| 7,288,174 B2 | 10/2007 | Cui et al. | |
| 7,291,256 B2 | 11/2007 | Teodorczyk et al. | |
| 7,338,639 B2 | 3/2008 | Burke et al. | |
| 7,390,667 B2 | 6/2008 | Burke et al. | |
| 7,407,811 B2 | 8/2008 | Burke et al. | |
| 7,431,820 B2 | 10/2008 | Hodges | |
| 7,452,457 B2 | 11/2008 | Burke et al. | |
| 7,488,601 B2 | 2/2009 | Burke et al. | |
| 7,597,793 B2 | 10/2009 | Burke et al. | |
| 7,749,371 B2 | 7/2010 | Guo et al. | |
| 7,771,583 B2 | 8/2010 | Diamond et al. | |
| 7,923,258 B2 | 4/2011 | Heller | |
| 8,101,065 B2 | 1/2012 | Chatelier et al. | |
| 8,551,320 B2 | 10/2013 | Hodges et al. | |
| 8,778,168 B2 | 7/2014 | Chatelier et al. | |
| 2002/0139692 A1 | 10/2002 | Tokunaga et al. | |
| 2002/0150896 A1 | 10/2002 | Polonsky et al. | |
| 2003/0109798 A1 | 6/2003 | Kermani | 600/547 |
| 2003/0155237 A1 | 8/2003 | Surridge et al. | |
| 2003/0180814 A1 | 9/2003 | Hodges et al. | |
| 2003/0201194 A1 | 10/2003 | Heller et al. | |
| 2003/0203498 A1 | 10/2003 | Neel et al. | |
| 2004/0079652 A1 | 4/2004 | Vreeke et al. | |
| 2004/0120848 A1 | 6/2004 | Teodorczyk | |
| 2004/0182703 A1 | 9/2004 | Bell et al. | |
| 2004/0203137 A1 | 10/2004 | Hodges et al. | |
| 2005/0004439 A1 | 1/2005 | Shin et al. | |
| 2006/0108236 A1 | 5/2006 | Kasielke et al. | |
| 2006/0134713 A1 | 6/2006 | Rylatt et al. | |
| 2006/0144704 A1* | 7/2006 | Ghesquiere | G01N 31/00 204/403.01 |
| 2006/0200017 A1 | 9/2006 | Monfre et al. | |
| 2006/0217602 A1 | 9/2006 | Abul-Haj et al. | |
| 2006/0231423 A1 | 10/2006 | Harding et al. | |
| 2007/0024287 A1 | 2/2007 | Graves et al. | |
| 2007/0034529 A1 | 2/2007 | Bard et al. | |
| 2007/0074977 A1 | 4/2007 | Guo et al. | |
| 2007/0131565 A1 | 6/2007 | Fujiwara et al. | |
| 2007/0154951 A1 | 7/2007 | Kermani | |
| 2007/0227912 A1 | 10/2007 | Chatelier et al. | |
| 2007/0231914 A1 | 10/2007 | Deng et al. | |
| 2007/0235346 A1 | 10/2007 | Popovich et al. | |
| 2008/0093230 A1 | 4/2008 | Diamond et al. | |
| 2008/0098802 A1 | 5/2008 | Burke et al. | |
| 2008/0105568 A1 | 5/2008 | Wu | |
| 2008/0173552 A1 | 7/2008 | Wu et al. | |
| 2008/0179197 A1 | 7/2008 | Wu | |
| 2008/0199894 A1 | 8/2008 | Galasso | |
| 2008/0214910 A1 | 9/2008 | Buck | |
| 2008/0274447 A1 | 11/2008 | Mecklenburg | |
| 2008/0293082 A1 | 11/2008 | Heller | |
| 2009/0000959 A1 | 1/2009 | Feldman et al. | |
| 2009/0005666 A1 | 1/2009 | Shin et al. | |
| 2009/0017483 A1 | 1/2009 | Yamaoka et al. | |
| 2009/0042306 A1 | 2/2009 | Reynolds et al. | |
| 2009/0045076 A1 | 2/2009 | Burke et al. | |
| 2009/0084687 A1* | 4/2009 | Chatelier | C12Q 1/001 205/792 |
| 2009/0089010 A1 | 4/2009 | Burke et al. | |
| 2009/0101523 A1 | 4/2009 | Deng | |
| 2009/0112478 A1 | 4/2009 | Mueller, Jr. et al. | |
| 2009/0157344 A1 | 6/2009 | Burke et al. | 702/104 |
| 2009/0292489 A1 | 11/2009 | Burke et al. | |
| 2009/0301899 A1* | 12/2009 | Hodges | G01N 27/3274 205/777.5 |
| 2010/0006452 A1 | 1/2010 | Hodges et al. | |
| 2010/0089775 A1 | 4/2010 | Chen et al. | |
| 2010/0173396 A1 | 7/2010 | Miller et al. | |
| 2010/0270178 A1 | 10/2010 | Guo et al. | |
| 2011/0073493 A1 | 3/2011 | Chatelier et al. | |
| 2011/0155584 A1 | 6/2011 | Chatelier et al. | |
| 2011/0155585 A1 | 6/2011 | Chatelier et al. | |
| 2011/0155589 A1 | 6/2011 | Chatelier et al. | |

FOREIGN PATENT DOCUMENTS

| | | |
|---|---|---|
| EP | 1 729 119 A1 | 12/2006 |
| EP | 1839571 A1 | 10/2007 |
| EP | 2 042 865 A2 | 4/2009 |
| EP | 2 138 841 A2 | 12/2009 |
| JP | 2000-509488 | 7/2000 |
| JP | 2003-240747 | 8/2003 |
| JP | 2009-85950 | 4/2009 |
| JP | 2009-294213 | 12/2009 |
| WO | WO 97/39343 | 10/1997 |
| WO | 03/069304 A2 | 8/2003 |
| WO | 2006/036833 A2 | 4/2006 |
| WO | WO-2008150436 A1 | 12/2008 |
| WO | 2009/140343 A1 | 11/2009 |

OTHER PUBLICATIONS

Australian Patent Examination Report for 2011309764; dated Sep. 19, 2013; 3 pages.
International Search Report/Written Opinion for PCT Application No. PCT/IB2011/002431; dated Mar. 6, 2012; 5 pages.
Australian Examiner's first report for Application No. 2010257395 dated Jun. 28, 2011 (2 Pages).
Australian Notice of Acceptance dated Oct. 27, 2011 for Application No. 2010257465 (3 Pages).
International Search Report and Written Opinion in PCT/IB2011/002472, dated Dec. 29, 2011 (12 Pages).
International Search Report and Written Opinion in PCT/US10/62629, dated Feb. 23, 2011.
Extended EP Search Report in EP 10252245.5, dated Jul. 7, 2011.
"WaveSense White Paper: Performance of the WaveSense KeyNote Blood Glucose Monitoring System Across 23 Lots of Test Strips", WaveSense, Mar. 2007 (Mar. 2007), XP002640744, URL: http://www.wavesense.info/uploads/pdf/23lotstudyKeyNote.pdf.pdf.
"WaveSense White Paper: Performance of the WaveSense KeyNote Blood Glucose Monitoring System Across 23 Lots of Test Strips", WaveSense, Mar. 2007 (Mar. 2007), XP002640744, URL: http://www.wavesense.info/uploads/pdf/23lotstudyKeyNote.pdf.pdf.

(56) References Cited

OTHER PUBLICATIONS

Chinese Office Action for CN 201180057658.0; dated Feb. 28, 2015, 12 pages.
Chinese Office Action and Search Report for CN 201180057658.0; dated Jun. 26, 2014; 17 pages.
Russian Office Action for RU 2013119959; dated Oct. 12, 2016; 15 pages.
Korean Office Action for KR 10-2013-7010604; dated Oct. 10, 2017; 4 pages.
Canadian Office Action and Examination Search Report for CA 2,811,851; dated May 23, 2017; 4 pages.
European Examination Report for EP 11 791 045.5; dated Apr. 10, 2018; 2 pages.
Russian Office Action for RU 2013119959; dated Feb. 15, 2016; 13 pages.
European Examination Report for EP 11 791 045.5; dated Oct. 15, 2018; 3 pages.

* cited by examiner

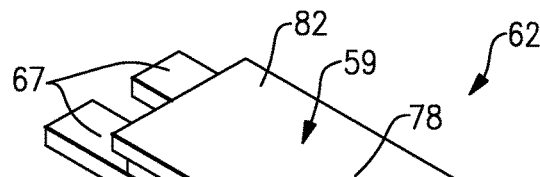
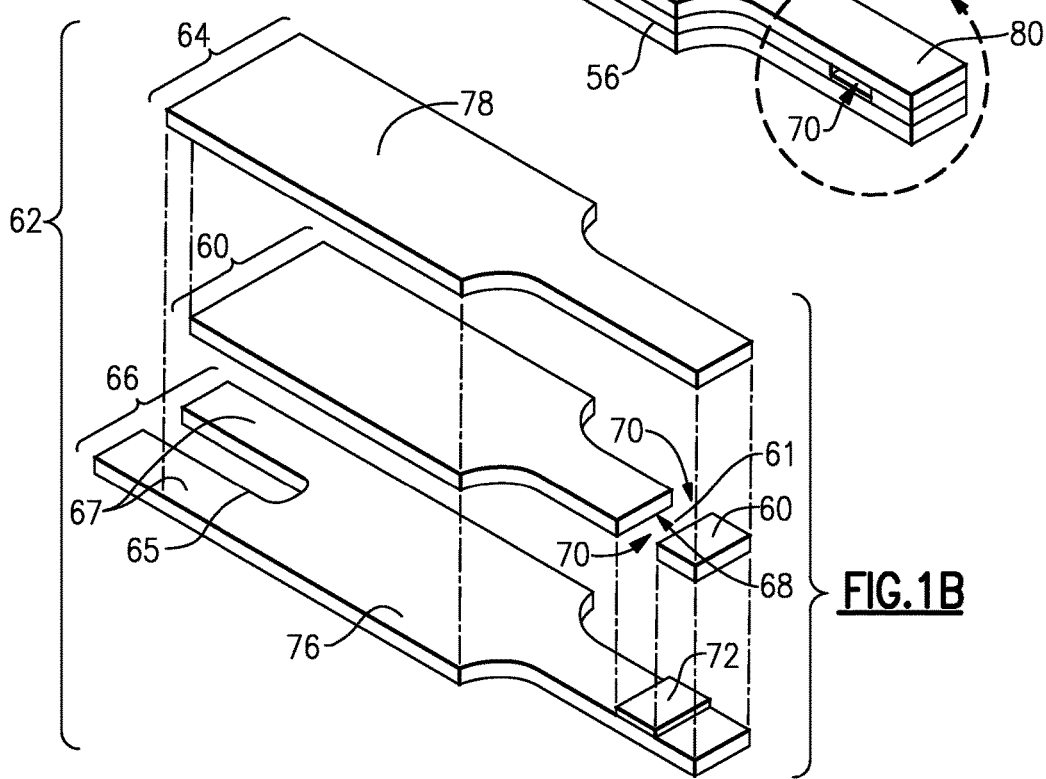
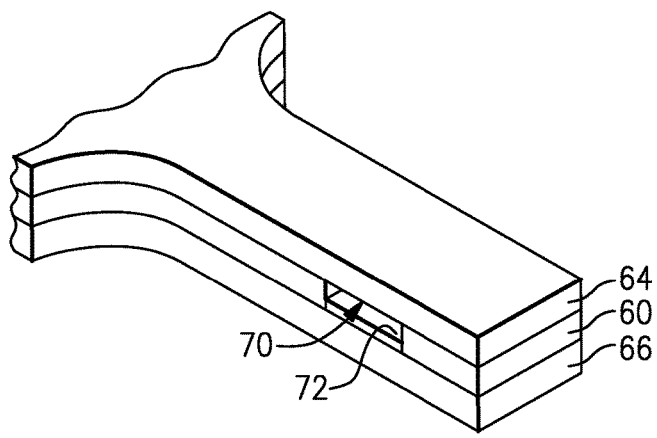

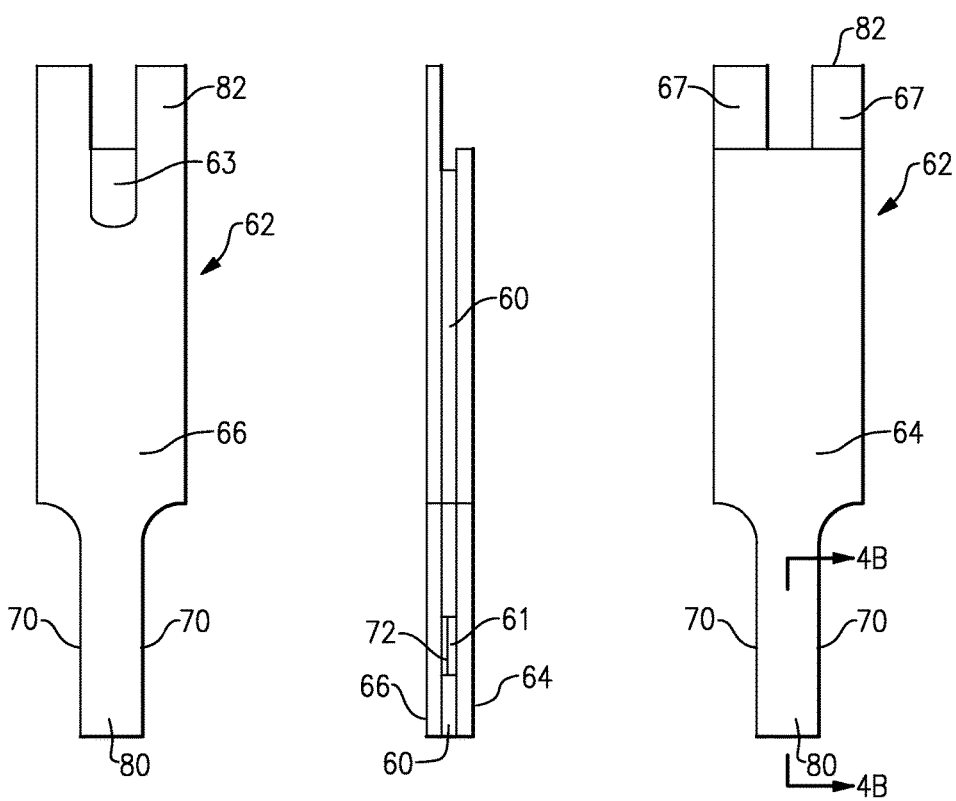
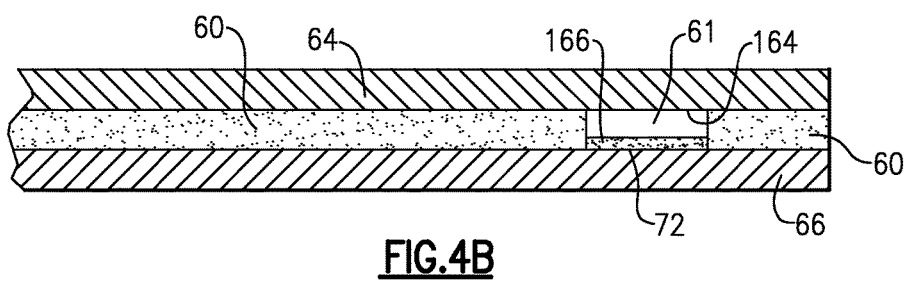

SYSTEMS AND METHODS OF DISCRIMINATING BETWEEN A CONTROL SAMPLE AND A TEST FLUID USING CAPACITANCE

CROSS-REFERENCE TO RELATED APPLICATIONS

This application is a divisional application of U.S. patent application Ser. No. 12/895,067, filed Sep. 30, 2010, entitled "Systems and Methods of Discriminating Between a Control Sample and a Test Fluid Using Capacitance", the entirety of which application is hereby incorporated herein by reference.

FIELD

The system and method provided herein relates to the field of medical testing, in particular the detection of the presence and/or concentration of an analyte(s) within a sample (e.g., physiological fluids including blood).

BACKGROUND

Analyte concentration determination in physiological fluids (e.g., blood or blood derived products such as plasma) is of ever increasing importance in today's society. Such assays find use in a variety of applications and settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like.

A common method for analyte concentration determination assays is based on electrochemistry. In such methods, an aqueous liquid sample is placed into a sample reaction chamber in an electrochemical cell made up of at least two electrodes, i.e., a working electrode and a counter electrode, where the electrodes have an impedance that renders them suitable for amperometric or coulometric measurement. The component to be analyzed is allowed to react with a reagent to form an oxidizable (or reducible) substance in an amount proportional to the analyte concentration. The quantity of the oxidizable (or reducible) substance present is then estimated electrochemically and related to the analyte concentration in the sample.

An automated device, e.g., an electrochemical test meter is typically employed for determining the concentration of the analyte in the sample. Many test meters advantageously allow for an analyte concentration, and usually a plurality of analyte concentrations, to be stored in the memory of the meter. This feature provides the user with the ability to review analyte concentration levels over a period of time, often times as an average of previously collected analyte levels, where such averaging is performed according to an algorithm associated with the meter. However, to ensure that the system is functioning properly, the user will occasionally perform a test using a control fluid instead of a blood sample. Such control fluids (also referred to as control solutions) are generally aqueous solutions having a known concentration of glucose. The user can perform a test with the control solution and compare the displayed results with the known concentration to determine if the system is functioning properly. However, once the control solution test is performed, the glucose concentration of the control fluid is stored in the memory of the meter. Thus, when a user seeks to review previous tests and/or the average concentration of previous test results, the results may be skewed to the concentration of the control fluid analyte level.

Thus, it is desirable to be able to distinguish control solutions and sample fluids during a test. One option is to manually flag the fluids as either control or test fluids. However automatic flagging would be preferable since it minimizes user interaction and increases ease-of-use.

As such, there is continued interest in the development of new methods and devices for use in the determination of analyte concentrations in a sample. Of particular interest would be the development of such methods and devices that include the ability to automatically flag a sample as a control fluid or test fluid and to store or exclude measurements accordingly. Of particular interest would be the development of such methods that are suitable for use with electrochemical based analyte concentration determination assays.

SUMMARY

Various aspects of a system and method for distinguishing between an aqueous non-blood sample (e.g., a control solution) and a blood sample are provided herein. In one such aspect, the methods include using an electrochemical cell in which a potential is applied and a current is measured. Further described herein are electrochemical methods and systems for distinguishing between blood samples and non-blood samples.

In one embodiment, a method for distinguishing between a blood sample and a non-blood sample is disclosed. The method includes introducing a sample into an electrochemical cell having first and second electrodes and applying a first test potential between the first electrode and the second electrode. A resulting first current transient is then measured. A second test potential is applied between the first electrode and the second electrode and a second current transient is then measured. A capacitance can also be measured, as will be discussed in more detail below. The method can also include applying a third test potential between the first electrode and the second electrode, and measuring a third current transient.

Based on the first current transient, a first reference value related to the quantity of redox species in the sample is calculated. In addition, based on the current values measured during the second and third current transients, a second reference value related to reaction kinetics is calculated. The second reference value can be a function of a percent completion of a chemical reaction. For example, the second reference value can be a residual reaction index calculated based upon at least one current value from the second current transient and at least one current value from the third current transient. In one aspect, the residual reaction index is calculated based upon a ratio of a second current value and a third current value. The first and second reference values can then be used to determine whether the sample is a non-blood sample or a blood sample. The non-blood sample can include a control solution or some other sample such as a beverage (e.g., a sports drink such as Gatorade®).

In one aspect, a capacitance index related to a measured capacitance is calculated. The capacitance index, for example, can be proportional to a measured capacitance of the electrochemical cell when a sample is introduced. In some embodiments, the capacitance index can be proportional to the measured capacitance and an average capacitance of electrochemical cells of the same type. For example, the capacitance index can be a ratio of an average capacitance of electrochemical cells of the same type and the measured capacitance. In some embodiments, a third reference value can be calculated by multiplying the first reference value by the capacitance index. The third reference value can then be used in combination with the second reference value to determine whether a sample is a non-blood sample or a blood sample.

In another aspect, the method can perform the step of measuring a concentration of an analyte in the sample. If the sample is found to be a blood sample, the measured concentration can be stored. Conversely, if the sample is found to be a non-blood sample, the measured concentration can be flagged, stored separately, and/or discarded.

In one embodiment, an inequality can be used to determine if the sample is a non-blood sample or a blood sample. For example, an equation representing an empirically derived discrimination line can be used to evaluate the second and third reference values.

In another aspect, an open-circuit potential is applied to the electrochemical cell before the step of applying the first test potential. In addition, an open-circuit potential can be applied after the step of applying the first test potential.

Further described herein is a system for distinguishing between a blood sample and a non-blood sample. In one embodiment, the system can include a test strip and a test meter. The test strip includes electrical contacts for mating with the test meter and an electrochemical cell. The test meter includes a processor configured to receive current data from the test strip, and data storage containing discrimination criteria so that a blood sample can be distinguished from a non-blood sample based on a first reference value and a second reference value. In some embodiments, a capacitance index related to a measured capacitance can be calculated. The capacitance index, for example, can be proportional to a measured capacitance of the electrochemical cell when a sample is introduced. In some embodiments, the capacitance index can be proportional to the measured capacitance and an average capacitance of electrochemical cells of the same type. For example, the capacitance index can include a ratio of an average capacitance of electrochemical cells of the same type and the measured capacitance. In some embodiments, a third reference value can be calculated by multiplying the first reference value by the capacitance index. The third reference value can then be used in combination with the second reference value to determine whether a sample is a non-blood sample or a blood sample. A discrimination criterion that separates data representing a blood sample from a non-blood sample can be derived from the second reference value and the third reference value. For example, the discrimination criterion can include an empirically derived discrimination line. The system can further include a non-blood sample (e.g., a control solution) that is substantially devoid of redox species. Still further described herein is a method for calculating a discrimination criterion. The discrimination criterion can be programmed into a test meter for distinguishing between a blood sample and a non-blood sample. In one embodiment, the method includes calculating a first reference value and a second reference value for a plurality of aqueous non-blood samples, calculating a third reference value based on the first reference value, the third reference value being proportional to a capacitance index, and calculating a discrimination criterion based on the second reference value and the third reference value for the plurality of non-blood samples. For example, the capacitance index can be a ratio of an average capacitance of electrochemical cells of the same type and a measured capacitance of the electrochemical cell. For another example, the first reference value is representative of anti-oxidant concentration and the second reference value is representative of reaction kinetics.

In one aspect, a method is provided for distinguishing between a blood sample and an aqueous non-blood sample. The method includes (a) introducing a sample into an electrochemical cell wherein the cell can include (i) two electrodes in a spaced apart relationship and (ii) a reagent. The method can further include the steps of (b) applying a first test potential, having a first polarity, between the electrodes, and measuring cell current; (c) measuring a capacitance of the electrochemical cell; (d) summing at least two current values measured during the first test potential to generate a first reference value, the first reference value being proportional to a concentration of redox species in the test liquid; (e) calculating a capacitance index related to the measured capacitance; and (f) using the capacitance index and the first reference value to distinguish between a blood sample and an aqueous non-blood sample. The method can further include a step of calculating a second reference value related to reaction kinetics and using the capacitance index, the first reference value, and the second reference value to distinguish between a blood sample and an aqueous non-blood sample. For example, the second reference value can be a function of a percent completion of a chemical reaction, which can also be referred to as a residual reaction index. In some exemplary embodiments, the capacitance index can be calculated as a ratio of an average capacitance of electrochemical cells of the same type and the measured capacitance. The method can also include the step of calculating a third reference value by multiplying the first reference value by the capacitance index. The third reference value can then be used in combination with the second reference value to determine whether a sample is a non-blood sample or a blood sample. In some embodiments, the aqueous non-blood sample can be a control solution.

The various reference values mentioned above can be determined and/or calculated in various manners. For example, the first reference value can be proportional to the concentration of redox species in the sample, the first reference value can be calculated based upon at least one current value from the first current transient, and/or the first reference value can be calculated based upon a summation of current values measured during the first current transient. In an embodiment wherein the first reference value can be calculated based upon a summation of current values measured during the first current transient, the summation can be represented by an equation, the equation being $$i_{sum} = \sum_{t=n}^{M} i(t),$$

where t is a time and $i_{sum}$ is the summation of current values during a time interval from a time n to a time M. The time interval from n to M can vary. For example, in one embodiment, the time interval can be for a time in the range of about 0.05 seconds to about 1.0 second.

In other embodiments, the second reference value can also be calculated or determined in various manners. For example, the second reference value can be based upon at least one current value from the second current transient and at least one current value from the third current transient, or the second reference value can be based upon a second current value at about the end of the second current transient and a third current value at about the beginning of the third current transient. In other embodiments, the second reference value can be based upon a ratio of the second current value and the third current value wherein the ratio can be represented by an equation, the equation being $$\text{ratio} = \frac{i_2}{i_3},$$

where $i_2$ is the second current value and $i_3$ is the second current value. For example, in one embodiment, the second current value can be measured at about 3.8 seconds and the third current value can be measured at about 4.15 seconds.

In various embodiments of the method, various orientations and/or configurations of various components of a system can be utilized. For example, in one embodiment, the first electrode and the second electrode can have an opposing face arrangement wherein a reagent layer can be disposed on the first electrode and not disposed on the second electrode. In another embodiment, the first electrode and the second electrode can have a co-planar arrangement with a reagent layer disposed on the first electrode and not disposed on the second electrode.

Various embodiments of the method can also include various additional or optional steps. For example, in one embodiment, the method can include the step of measuring a concentration of an analyte wherein, for example, if the sample is found to be a control solution the analyte concentration associated with the control sample is flagged. Additionally, in one embodiment, above-identified step can further include using an inequality to determine if the sample is a control solution or a blood sample. In another embodiment, the above-identified step can further include comparing the third reference value to a pre-determined threshold value, and comparing the second reference value to a pre-determined threshold function (e.g., an equation which is a function of the first reference value) to determine if the sample is a control solution or a blood sample.

In various embodiments, the above-mention discrimination criteria can be derived from various sources. For example, in one embodiment, the discrimination criteria can be derived from a first reference value that is representative of the redox concentration in the sample multiplied by a capacitance index, and a second reference value that is representative of the rate of reaction of the sample with the reagent. In some embodiments, the capacitance index related to a measured capacitance is calculated. The capacitance index, for example, can be proportional to a measured capacitance of the electrochemical cell when a sample is introduced. In some embodiments, the capacitance index can be proportional to the measured capacitance and an average capacitance of electrochemical cells of the same type. For example, the capacitance index can be a ratio of a known capacitance, e.g., an average capacitance of electrochemical cells of the same type, to a measured capacitance. In another embodiment, the discrimination criteria can include an empirically derived discrimination line.

BRIEF DESCRIPTION OF THE DRAWINGS

Various features of the present disclosure are set forth with particularity in the appended claims. A better understanding of such features can be obtained by reference to the following detailed description that sets forth illustrative, non-limiting embodiments and the accompanying drawings of which:

FIG. 1A is a perspective view of an exemplary test strip;
FIG. 1B is an exploded perspective view of the test strip of FIG. 1A;
FIG. 1C is a perspective view of a distal portion of the test strip of FIG. 1A;
FIG. 2 is a bottom plan view of the test strip of FIG. 1A;
FIG. 3 is a side plan view of the test strip of FIG. 1A;
FIG. 4A is a top plan view of the test strip of FIG. 1A;
FIG. 4B is a partial side view of the distal portion of the test strip consistent with arrows 4B-4B of FIG. 4A.

DETAILED DESCRIPTION

Figure 5:
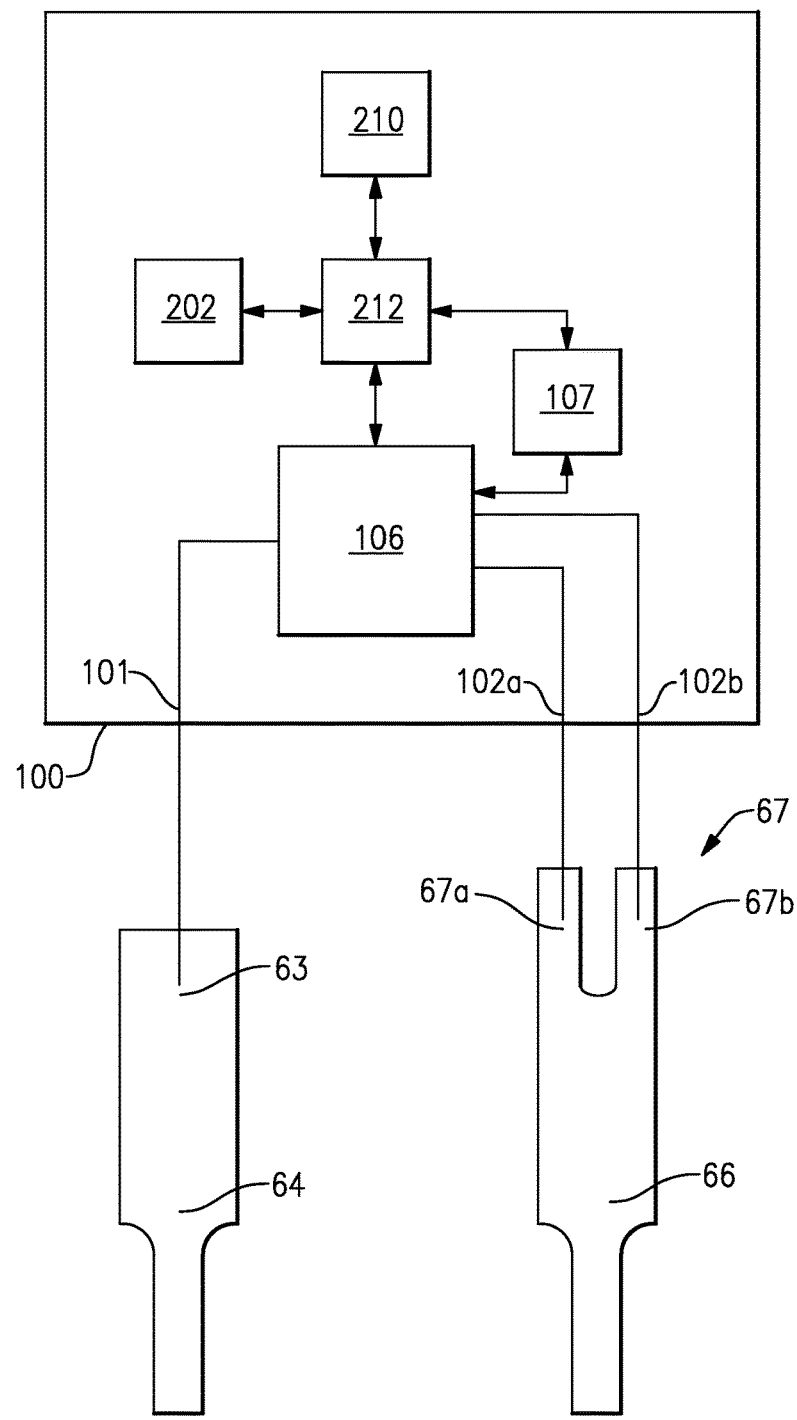
FIG. 5 is a simplified schematic showing a test meter electrically interfacing with the test strip contact pads.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. As used herein, the terms "about" or "approximately" for any numerical values or ranges indicate a suitable tolerance that allows the part or collection of components to function for its intended purpose as described herein.

The presently disclosed systems and methods are suitable for use in the determination of a wide variety of analytes in a wide variety of samples, and are particularly suited for use in the determination of analytes in whole blood or derivatives thereof, where an analyte of particular interest is glucose. In one aspect, the present disclosure provides various embodiments of a method for determining whether a sample applied to a test strip is an aqueous non-blood sample (e.g., a control solution) or a blood sample. In one such embodiment, at least two characteristics are used to distinguish between a blood sample and a non-blood sample. This description will focus on distinguishing between blood samples and control solutions. However, the systems and methods provided herein are equally applicable to distinguishing blood samples from any of a variety of non-blood samples (e.g., beverages including sports drinks such as Gatorade®).

The methods provided herein may be used, in principle, with any type of electrochemical cell having spaced apart first and second electrodes and a reagent layer. For example, an electrochemical cell can be in the form of a test strip. In one aspect, the test strip includes two opposing electrodes separated by a thin spacer layer, where these components define a sample reaction chamber or zone in which is located a reagent layer. Applicants note that other types of test strips, including, for example, test strips with co-planar electrodes could also be used with the methods described herein.

FIGS. 1A-4B show various views of an exemplary test strip 62 suitable for use with the methods described herein. As shown, the test strip 62 can include an elongate body extending from a proximal end 80 to a distal end 82, and having lateral edges 56, 58. The proximal portion of the body 59 can include a sample reaction chamber 61 having multiple electrodes 164, 166 and a reagent 72, while the distal portion of the test strip body 59 can include features configured for electrically communicating with a test meter. In use, physiological fluid or a control solution can be delivered to the sample reaction chamber 61 for electrochemical analysis.

In the illustrative embodiment, the test strip 62 can include a first electrode layer 66 and a second electrode layer 64, with a spacer layer 60 positioned therebetween. The first electrode layer 66 can provide a first electrode 166 and a first connection track 76 for electrically connecting the first electrode 166 to a first electrical contact 67. Similarly, the second electrode layer 64 can provide a second electrode 164 and a second connection track 78 for electrically connecting the second electrode 164 with a second electrical contact 63.

In one embodiment, the sample reaction chamber 61 is defined by the first electrode 166, the second electrode 164, and a spacer 60 as shown in FIGS. 1A-4B. Specifically, the first electrode 166 and the second electrode 164 define, respectively, the bottom and top of the sample reaction chamber 61. A cutout area 68 of the spacer 60 can define the side walls of the sample reaction chamber 61. In one aspect, the sample reaction chamber 61 can further include an number of ports 70 that provide a sample inlet and/or a vent. For example, one of the ports can provide a fluid sample ingress and the other port can act as a vent.

The sample reaction chamber 61 can have a small volume. For example, the volume can range from about 0.1 microliters to about 5 microliters, preferably about 0.2 microliters to about 3 microliters, and more preferably about 0.3 microliters to about 1 microliter. As will be appreciated by those skilled in the art, the sample reaction chamber 61 can have various other such volumes. To provide the small sample volume, the cutout 68 can have an area ranging from about 0.01 $cm^2$ to about 0.2 $cm^2$, preferably about 0.02 $cm^2$ to about 0.15 $cm^2$, and more preferably about 0.03 $cm^2$ to about 0.08 $cm^2$. Similarly, those skilled in the art will appreciate that the volume cutout 68 can be of various other such areas. In addition, the first and second electrode 166, 164 can be spaced in the range of about 1 micron to about 500 microns, preferably in the range of about 10 microns to about 400 microns, and more preferably in the range of about 40 microns to about 200 microns. In other embodiments, such a range can vary in the range of various other values. The close spacing of the electrodes can also allow redox cycling to occur, where oxidized mediator generated at the first electrode 166, can diffuse to the second electrode 164 to become reduced, and subsequently diffuse back to the first electrode 166 to become oxidized again.

At the distal end of the test strip body 59, a first electrical contact 67 can be used to establish an electrical connection to a test meter. A second electrical contact 63 can be accessed by the test meter through a U-shaped notch 65 as illustrated in FIG. 2. Applicants note that the test strip 62 can include a variety of alternative electrical contact configured for electrically connecting to a test meter. For example, U.S. Pat. No. 6,379,513, the entirety of which is hereby incorporated herein by reference, discloses an electrochemical cell connection means.

In one embodiment, the first electrode layer 66 and/or the second electrode layer 64 can be a conductive material formed from materials such as gold, palladium, carbon, silver, platinum, tin oxide, iridium, indium, and combinations thereof (e.g., indium doped tin oxide). In addition, the electrodes can be formed by disposing a conductive material onto an insulating sheet (not shown) by various process such as, for example, a sputtering, electroless plating, or a screen printing process. In one exemplary embodiment, the second electrode layer 64 can be a sputtered gold electrode and the first electrode layer 66 can be a sputtered palladium electrode. Suitable materials that can be employed as the spacing layer 60 include various insulating materials, such as, for example, plastics (e.g., PET, PETG, polyimide, polycarbonate, polystyrene), silicon, ceramic, glass, adhesives, and combinations thereof.

A reagent layer 72 can be disposed within the sample reaction chamber 61 using a process such as slot coating, dispensing from the end of a tube, ink jetting, and screen printing. Such processes are described, for example, in the following U.S. Pat. Nos. 6,749,887; 6,869,411; 6,676,995; and 6,830,934, the entirety of each of these references being incorporated herein by reference. In one embodiment, the reagent layer 72 can include at least a mediator and an enzyme, and can be deposited onto the first electrode 166. Various mediators and/or enzymes are within the spirit and scope of the present disclosure. For example, suitable mediators include ferricyanide, ferrocene, ferrocene derivatives, osmium bipyridyl complexes, and quinone derivatives. Examples of suitable enzymes include glucose oxidase, glucose dehydrogenase (GDH) based on pyrroloquinoline quinone (PQQ) co-factor, GDH based on nicotinamide adenine dinucleotide (NAD) co-factor, and FAD-based GDH [E.C.1.1.99.10]. One exemplary reagent formulation, which would be suitable for making the reagent layer 72, is described in pending U.S. application Ser. No. 10/242,951, entitled, "Method of Manufacturing a Sterilized and Calibrated Biosensor-Based Medical Device", published as U.S. Published Patent Application No. 2004/0120848, the entirety of which is hereby incorporated herein by reference.

Either the first electrode 166 or the second electrode 164 can function as working electrode which oxidizes or reduces a limiting amount of mediator depending on the polarity of the applied test potential of the test meter. For example, if the current limiting species is a reduced mediator, it can be oxidized at the first electrode 166 as long as a sufficiently positive potential was applied with respect to the second electrode 164. In such a situation, the first electrode 166 performs the function of the working electrode and second electrode 164 performs the function of a counter/reference electrode. It should be noted that unless otherwise stated for test strip 62, all potentials applied by test meter 100 will hereinafter be stated with respect to second electrode 164.

Similarly, if a sufficiently negative potential is applied with respect to the second electrode 164, then the reduced mediator can be oxidized at the second electrode 164. In such a situation, the second electrode 164 can perform the function of the working electrode and the first electrode 166 can perform the function of the counter/reference electrode.

A first step in an embodiment of the presently disclosed method can include introducing a quantity of the fluid sample of interest into the test strip 62, which includes the first electrode 166, the second electrode 164 and a reagent layer 72. The fluid sample can be whole blood or a derivative or fraction thereof, or a control solution. The fluid sample, e.g., blood, can be dosed into the sample reaction chamber 61 via the port 70. In one aspect, the port 70 and /or the sample reaction chamber 61 can be configured such that capillary action causes the fluid sample to fill the sample reaction chamber 61.

FIG. 5 provides a simplified schematic of a test meter 100 interfacing with a first electrical contact 67 and a second electrical contact 63, which are in electrical communication with the first electrode 166 and the second electrode 164, respectively, of the test strip 62. The test meter 100 can be configured to electrically connect to the first electrode 166 and the second electrode 164 via a first electrical contact 67 and a second electrical contact 63, respectively (as shown in FIGS. 2 and 5). As will be appreciated by those skilled in the art, a variety of test meters can be used with the method described herein. However, in one embodiment, the test meter includes at least a processor configured for performing calculations capable of discriminating between blood and a control sample, as well as configured for data sorting and/or storage. The microprocessor can be in the form of a mixed signal microprocessor (MSP) such as, for example, the Texas Instrument MSP 430. The TI-MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit.

As illustrated in FIG. 5, an electrical contact 67 can include two prongs 67a, 67b. In one exemplary embodiment, the test meter 100 separately connects to the prongs 67a, 67b, such that when the test meter 100 interfaces with a test strip 62 a circuit is completed. The test meter 100 can measure the resistance or electrical continuity between the prongs 67a, 67b to determine whether the test strip 62 is electrically connected to the test meter 100. Applicants note that the test meter 100 can use a variety of sensors and circuits to determine when the test strip 62 is properly positioned with respect to the test meter 100.

In one embodiment, test meter 100 can apply a test potential and/or a current between first electrical contact 67 and second electrical contact 63. Once test meter 100 recognizes that strip 62 has been inserted, test meter 100 turns on and initiates a fluid detection mode. In one embodiment, the fluid detection mode causes test meter 100 to apply a constant current of 1 microampere between first electrode 166 and second electrode 164. Because test strip 62 is initially dry, test meter 100 measures a maximum voltage, which is limited by the hardware within test meter 100. However, once a user introduces a fluid sample onto inlet 70, this causes sample reaction chamber 61 to become filled. When the fluid sample bridges the gap between first electrode 166 and second electrode 164, test meter 100 will measure a decrease in measured voltage (e.g., as described in U.S. Pat. No. 6,193,873, the entirety of which being incorporated herein by reference), which is below a predetermined threshold causing test meter 100 to automatically initiate the glucose test.

It should be noted that the measured voltage may decrease below a pre-determined threshold when only a fraction of the sample reaction chamber 61 has been filled. A method of automatically recognizing that a fluid was applied does not necessarily indicate that the sample reaction chamber 61 has been completely filled, but can only confirm a presence of some amount of fluid in the sample reaction chamber 61. Once the test meter 100 determines that a fluid has been applied to test strip 62, a short, but non-zero amount of time may still be required to allow the fluid to completely fill the sample reaction chamber 61.

Figure 6:
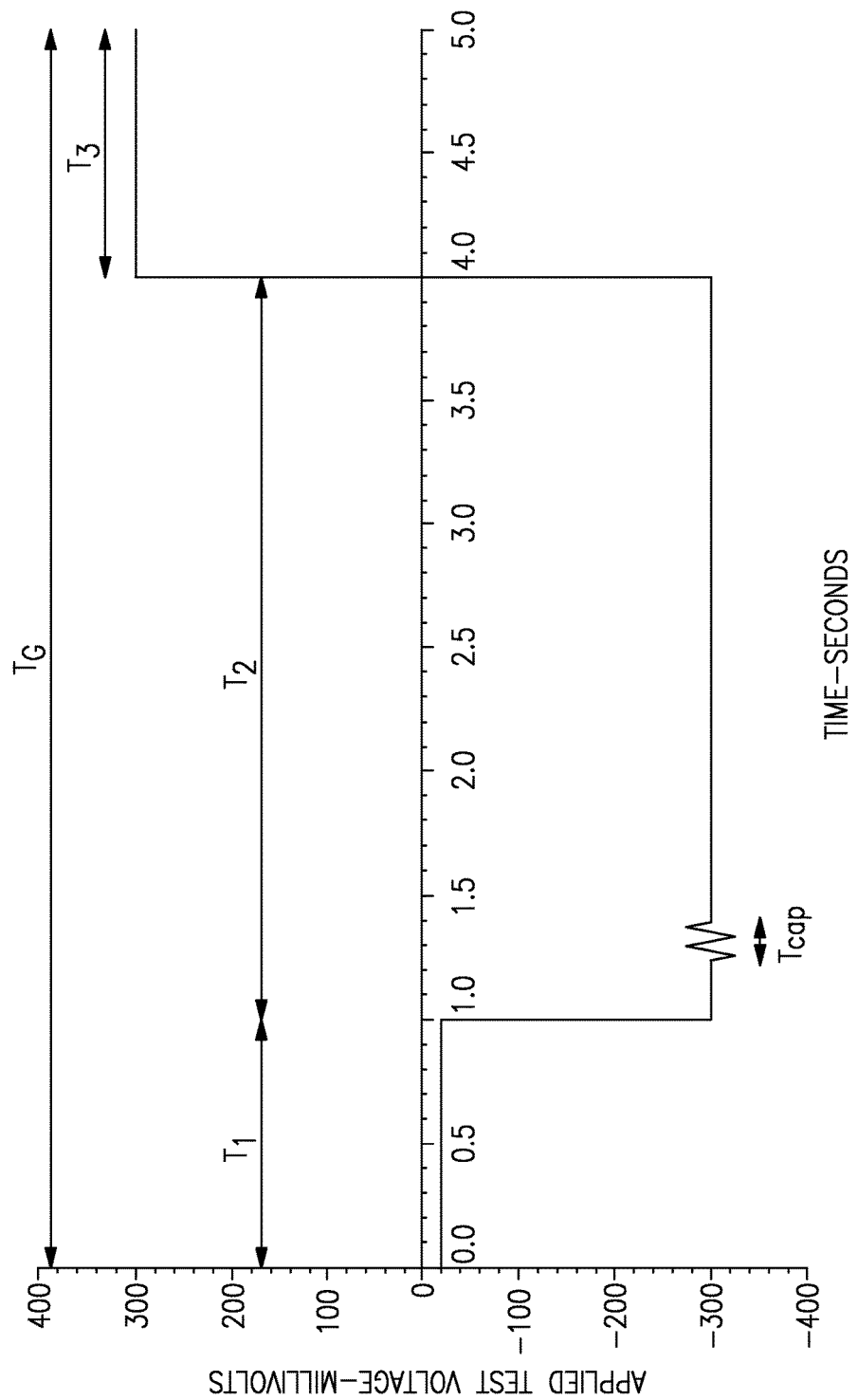
FIG. 6 shows a test voltage waveform in which the test meter applies a plurality of test voltages for prescribed time intervals.

In one embodiment, once the test meter 100 has determined that a fluid has been introduced (e.g., dosed) onto the test strip 62, a test meter 100 can perform a glucose test by applying a plurality of test potentials to the test strip 62 for prescribed intervals as illustrated by FIG. 6. A glucose test time interval $T_G$ represents an amount of time to perform the glucose test (but not necessarily all the calculations associated with the glucose test) where the glucose test time interval $T_G$ can include a first test potential $E_1$ for a first test potential time interval $T_1$, a second test potential $E_2$ for a second test potential time interval $T_2$, and a third test potential $E_3$ for a third test potential time interval $T_3$. Further, as illustrated in FIG. 6, the second test potential time interval $T_2$ can include a constant direct-current (DC) test voltage component and a superimposed alternating (AC), or oscillating, test voltage component. The superimposed alternating test voltage component can be applied for a time interval indicated by $T_{cap}$. The time intervals shown in FIG. 6 are only examples and can range as more fully described herein. The glucose test time interval $T_G$ can range, for example, from about 1 second to about 5 seconds.

As discussed above, either the first electrode 166 or the second electrode 164 can function as working electrode which oxidizes or reduces a limiting amount of mediator depending on the polarity of the applied test potential of the test meter. It should be noted that unless otherwise stated all potentials applied by test meter 100 will hereinafter be stated with respect to second electrode 164. However, applicants note that the test potentials applied by test meter 100 can also be stated with respect to the first electrode 166, in which case the polarity of the test potentials and measured currents discussed below would be reversed.

The plurality of test current values measured during the first, second, and third test potential time intervals may be performed at a frequency ranging from about 1 measurement per approximately 1 nanosecond to about one measurement per approximately 100 milliseconds. Applicants note that names "first," "second," and "third" are chosen for convenience and do not necessarily reflect the order in which the test potentials are applied. For instance, an embodiment can have a potential waveform where the third test voltage can be applied before the application of the first and second test voltage. While an embodiment using three test voltages in a serial manner is described, applicants note that the glucose test can include different numbers of open-circuit and test voltages. Applicants further note that the glucose test time interval can include any number of open-circuit potential time intervals. For example, the glucose test time interval could include only two test potential time intervals and/or open circuit potential time intervals before and/or after one or more test potential time intervals. In another exemplary embodiment, the glucose test could include an open-circuit for a first time interval, a second test voltage for a second time interval, and a third test voltage for a third time interval.

As shown in FIG. 6, the test meter 100 may apply a first test potential $E_1$ (e.g., about −20 mV as illustrated in FIG. 6) for a first test potential time interval $T_1$ (e.g., in the range of about 0 to about 1 second). For example, the first test potential time interval $T_1$ can start at zero (0) seconds and can end after a period of time in the range of about 0.1 seconds to about 3 seconds, about 0.2 seconds to about 2 seconds, or about 0.3 seconds to about 1 seconds at an initiation point of zero (0) seconds in FIG. 6. The first test potential time interval $T_1$ may be sufficiently long so that the sample reaction chamber 61 can fully fill with sample and also so that the reagent layer 72 can at least partially dissolve or solvate.

In one embodiment, the test meter 100 can apply a first test potential $E_1$ between the electrodes for a duration between when the meter can detect that the strip is filling with sample and before a second test potential $E_2$ is applied. In one aspect, the test potential $E_1$ is small. For example, the magnitude of the first test potential can be in the range of about 1 to about 100 mV preferably in the range of about 5 mV to about 50 mV and most preferably in the range of about 10 mV to about 30 mV. Applicants note that the polarity of the first test potential can expressed as either a positive or negative value. For example, the first test potential can either be expressed as a negative test potential with respect to the second electrode 164, or as a positive test potential with respect to the first electrode 166. The smaller potential perturbs the reduced mediator concentration gradient to a lesser extent compared to applying a larger potential difference, but is still sufficient to obtain a measure of the oxidizable substances in the sample. The test potential $E_1$ can be applied for a portion of the time between detection of fill and when the second test potential $E_2$ is applied or can be applied for the whole of that time period. If the test potential $E_1$ is to be used for a portion of the time then an open-circuit could be applied for the remaining portion of the time. The combination of any number of open-circuit and small voltage potential applications, their order and times applied is not critical in this embodiment, can be applied as long as the total period for which the small potential $E_1$ is applied is sufficient to obtain a current measurement indicative of the presence and/or quantity of oxidizable substances present in the sample. In a preferred embodiment, the small potential $E_1$ is applied for substantially the entire period between when a fill is detected and when the second test potential $E_2$ is applied.

During the first time interval $T_1$, the test meter 100 measures the resulting first current transient, which can be referred to as $i_a(t)$. A current transient represents a plurality of current values measured by a test meter during a particular test potential time interval. The first current transient can be an integral of current values over the first test potential time interval, or an average or single current value measured during the first test potential time interval multiplied by the time interval of the first test potential time interval. In some embodiments, the first current transient can include current values measured over various time intervals during the first test potential time interval. In one embodiment, the first current transient $i_a(t)$ can be measured for a time in the range of about 0.05 seconds to about 1.0 second. In other embodiments, the first current transient $i_a(t)$ can be measured for other desired time ranges, such as a time in the range of about 0.1 seconds to about 0.5 or in the range of about 0.1 seconds to about 0.2 seconds. As discussed below, a portion or all of the first current transient can be used in the methods described herein to determine whether a control solution or a blood sample was applied to the test strip 62. The magnitude of the first transient current is affected by the presence of easily oxidizable substances in the sample. Blood usually contains endogenous and exogenous compounds that are easily oxidized at second electrode 164. Conversely, the control solution can be formulated such that it does not contain oxidizable compounds. However, blood sample composition can vary and the magnitude of the first current transient for high viscosity blood samples will typically be smaller than low viscosity samples (in some cases even less than the control solution samples). Also an incomplete fill will cause the effective area of the first electrode 166 and the second electrode 164 to decrease which in turn can cause the first current transient to decrease. Thus, the presence of oxidizable substances in a sample, by itself, is not always a sufficient discriminatory factor because of variations in blood samples.

Once the first time interval $T_1$ time has elapsed, the test meter 100 can apply a second test potential $E_2$ between the first electrode 166 and the second electrode 164 (e.g., about −300 mV as illustrated in FIG. 6) for a second test potential time interval $T_2$ (e.g., about 3 seconds as illustrated in FIG. 6). The second test potential $E_2$ may be a value sufficiently negative of the mediator redox potential so that a limiting oxidation current occurs at the second electrode 164. For example, when using ferricyanide and/or ferrocyanide as the mediator, the second test potential $E_2$ can range from about −600 mV to about zero mV, preferably range from about −600 mV to about −100 mV, and more preferably be about −300 mV. Likewise, the time interval indicated as $t_{cap}$ in FIG. 6 may also last over a range of times, but in one exemplary embodiment it has a duration of about 20 milliseconds. In one exemplary embodiment, the superimposed alternating test voltage component is applied after about 0.3 seconds to about 0.32 seconds after the application of the second test voltage $V_2$, and induces two cycles of a sine wave having a frequency of about 109 Hz with an amplitude of about +/−50 mV. During the second test potential time interval $T_2$, the test meter 100 can measure a second current transient $i_b(t)$.

The second test potential time interval $T_2$ may be sufficiently long to monitor the rate of generation of reduced mediator (e.g., ferrocyanide) in the sample reaction chamber 61 based on the magnitude of a limiting oxidation current. The reduced mediator may be generated by a series of chemical reactions in the reagent layer 72. During the second test potential time interval $T_2$, a limiting amount of reduced mediator is oxidized at the second electrode 164 and a non-limiting amount of oxidized mediator is reduced at the first electrode 166 to form a concentration gradient between the first electrode 166 and the second electrode 164. As will be described, the second test potential time interval $T_2$ should be sufficiently long so that a sufficient amount of ferricyanide can be generated at the second electrode 164. A sufficient amount of ferrocyanide may be required at the second electrode 164 so that a limiting current can be measured for oxidizing ferrocyanide at the first electrode 166 during the third test potential $E_3$. The second test potential time interval $T_2$ can range from about 0 seconds to about 60 seconds and preferably range from about 1 second to about 10 seconds, and most preferably range from about 2 seconds to about 5 seconds.

Figure 7:
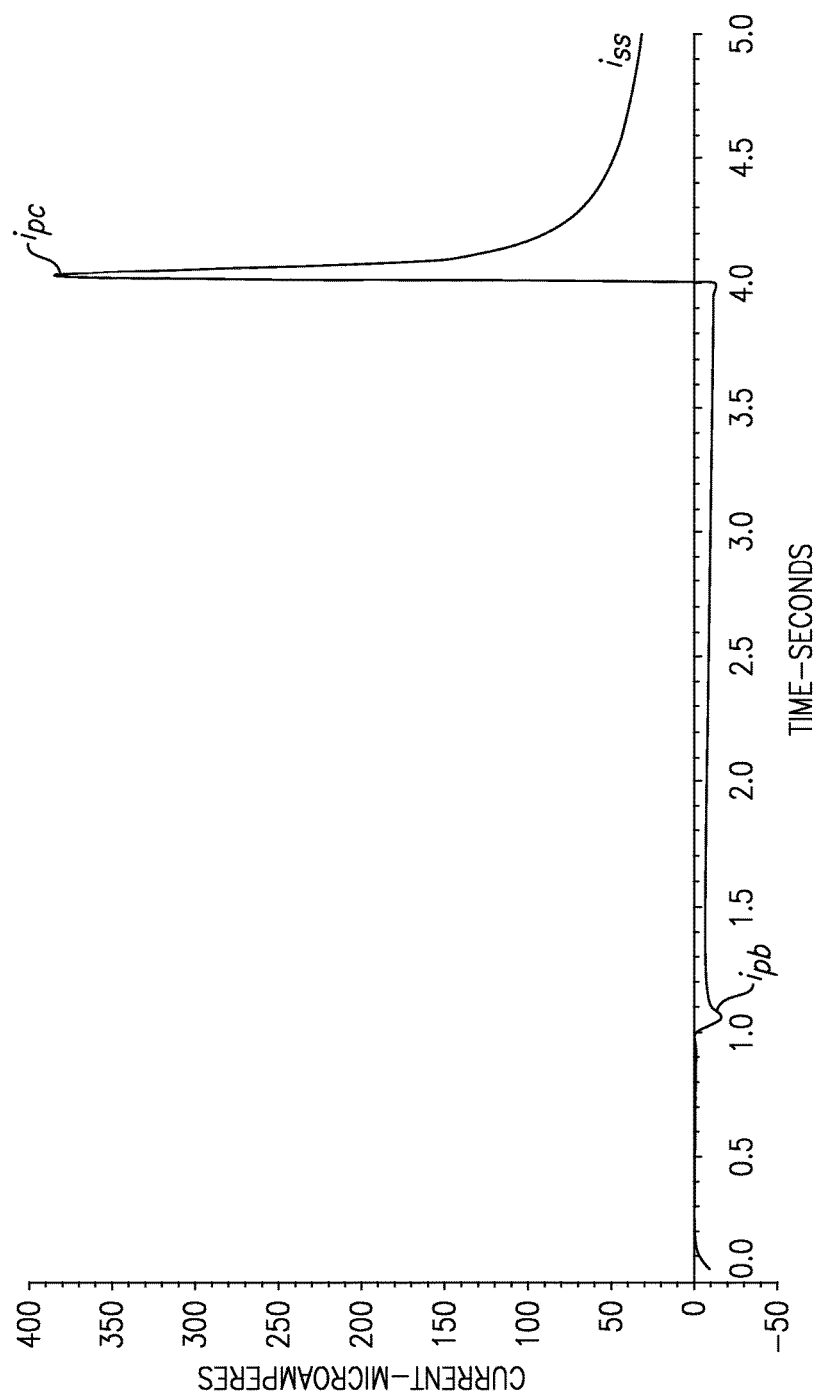
FIG. 7 shows a test current transient generated with the test voltage waveform of FIG. 6.

FIG. 7 shows a relatively small peak $i_{pb}$ at the beginning of the second test potential time interval $T_2$ followed by a gradual increase of an absolute value of an oxidation current during the second test potential time interval (e.g., in the range of about 1 second to about 4 seconds). The small peak occurs due to an initial depletion of reduced mediator at about 1 second. The gradual increase in oxidation current is ascribed to the generation of ferrocyanide by reagent layer 72 followed by its diffusion to the second electrode 164.

After the second potential time interval $T_2$ has elapsed, the test meter 100 can apply a third test potential $E_3$ between the first electrode 166 and the second electrode 164 (e.g., about +300 as illustrated in FIG. 6) for a third test potential time interval $T_3$ (e.g., in the range of about 4 to about 5 seconds as illustrated in FIG. 6). During the third test potential time interval $T_3$, the test meter 100 can measure a third current transient, which may be referred to as $i_c(t)$. The third test potential $E_3$ may be a value sufficiently positive of the mediator redox potential so that a limiting oxidation current is measured at the first electrode 166. For example, when using ferricyanide and/or ferrocyanide as the mediator, the magnitude of the third test potential $E_3$ can range from about zero mV to about 600 mV, preferably range from about 100 mV to about 600 mV, and more preferably be about 300 mV.

The second test potential time interval $T_2$ and the third test potential time interval $T_3$ can each range from about 0.1 seconds to about 4 seconds. For the embodiment shown in FIG. 6, the second test potential time interval $T_2$ was about 3 seconds and the third test potential time interval $T_3$ was about 1 second. As mentioned above, an open circuit potential time period can be allowed to elapse between the second test potential $E_2$ and the third test potential $E_3$. Alternatively, the third test potential $E_3$ can be applied following the application of the second test potential $E_2$. Note that a portion of the first, second, or third current transient may be generally referred to as a cell current or a current value.

The third test potential time interval $T_3$ may be sufficiently long to monitor the diffusion of a reduced mediator (e.g., ferrocyanide) near the first electrode 166 based on the magnitude of the oxidation current. During the third test potential time interval $T_3$, a limiting amount of reduced mediator is oxidized at the first electrode 166 and a non-limiting amount of oxidized mediator is reduced at the second electrode 164. The third test potential time interval $T_3$ can range from about 0.1 seconds to about 5 seconds and preferably range from about 0.3 seconds to about 3 seconds, and most preferably range from about 0.5 seconds to about 2 seconds.

FIG. 7 shows a relatively large peak $i_{pc}$ at the beginning of the third test potential time interval $T_3$ followed by a decrease to a steady-state current. In one embodiment, the first test potential $E_1$ and the second test potential $E_2$ both have a first polarity, and the third test potential $E_3$ has a second polarity, which is opposite to the first polarity. However applicants note that the polarity of the first, second, and third test potentials can be chosen depending on the manner in which analyte concentration is determined and/or depending on the manner in which the test samples and control solutions are distinguished.

Capacitance Measurement

In some embodiments, a capacitance can be measured. The capacitance measurement can measure essentially an ionic double-layer capacitance resulting from the formation of ionic layers at the electrode-liquid interface. A magnitude of the capacitance can be used to determine whether a sample is control solution or a blood sample. For example, when a control solution is within the reaction chamber, the magnitude of the measured capacitance can be greater than the magnitude of the measured capacitance when a blood sample is in the reaction chamber. As will be discussed in more detail below, a measured capacitance can be used in various methods to distinguish between a control solution and a blood sample. For example, such methods can use the ratio of a measured capacitance to a known average capacitance measured when blood samples are loaded into electrochemical cells of the same type.

By way of non-limiting example, methods and mechanisms for performing capacitance measurements on test strips can be found in U.S. Pat. Nos. 7,195,704 and 7,199,594, each of which is hereby incorporated by reference in its entirety. In one exemplary method for measuring capacitance, a test voltage having a constant component and an oscillating component is applied to the test strip. In such an instance, the resulting test current can be mathematically processed, as described in further detail below, to determine a capacitance value.

Generally, when a limiting test current occurs at a working electrode having a well-defined area (i.e., an area not changing during the capacitance measurement), the most accurate and precise capacitance measurements in an electrochemical test strip can be performed. A well-defined electrode area that does not change with time can occur when there is a tight seal between the electrode and the spacer. The test current is relatively constant when the current is not changing rapidly due either to glucose oxidation or electrochemical decay. Alternatively, any period of time when an increase in signal, which would be seen due to glucose oxidation, is effectively balanced by a decrease in signal, which accompanies electrochemical decay, can also be an appropriate time interval for measuring capacitance.

An area of first electrode 166 can potentially change with time after dosing with the sample if the sample seeps in between the spacer 60 and the first electrode 166. In an embodiment of a test strip, reagent layer 72 can have an area larger than the cutout area 68 that causes a portion of the reagent layer 72 to be in between the spacer 60 and the first electrode layer 66. Under certain circumstances, interposing a portion of the reagent layer 72 in between the spacer 60 and the first electrode layer 66 can allow the wetted electrode area to increase during a test. As a result, a leakage can occur during a test that causes the area of the first electrode to increase with time, which in turn can distort a capacitance measurement.

In contrast, an area of second electrode 164 can be more stable with time compared to the first electrode 166 because there is no reagent layer in between the second electrode 164 and the spacer 60. Thus, the sample is less likely to seep in between the spacer 60 and the second electrode 164. A capacitance measurement that uses a limiting test current at the second electrode 164 can thus be more precise because the area does not change during the test.

As discussed above and as shown in FIG. 6, once liquid is detected in the test strip, first test potential $E_1$ (e.g., about −20 mV, as illustrated in FIG. 7) can be applied between the electrodes for about 1 second to monitor the fill behavior of the liquid and to distinguish between control solution and blood. In Equation 1, the test currents are used from about 0.05 to about 1 second. This first test potential $E_1$ can be relatively low such that the distribution of ferrocyanide in the cell is disturbed as little as possible by the electrochemical reactions occurring at the first and second electrodes.

A second test potential $E_2$ (e.g., about −300 mV, as illustrated in FIG. 6) having a larger absolute magnitude can be applied after the first test potential $E_1$ such that a limiting current can be measured at the second electrode 164. The second test potential $E_2$ can include an AC voltage component and a DC voltage component. The AC voltage component can be applied at a predetermined amount of time after the application of the second test potential $E_2$, and further, can be a sine wave having a frequency of about 109 Hertz and an amplitude of about +/−50 millivolts. In a preferred embodiment, the predetermined amount of time can range from about 0.3 seconds to about 0.4 seconds after the application of the second test potential $E_2$. Alternatively, the predetermined amount of time can be a time where a test current transient as a function of time has a slope of about zero. In another embodiment, the predetermined amount of time can be a time required for a peak current value (e.g., $i_{pb}$) to decay by about 50%. As for the DC voltage component, it can be applied at a beginning of the first test potential. The DC voltage component can have a magnitude sufficient to cause a limiting test current at the second electrode such as, for example, about −300 mV with respect to the second electrode.

Consistent with FIG. 4B, the reagent layer 72 is coated onto the first electrode 166, not onto the second electrode 164, which causes the magnitude of the absolute peak current $i_{pb}$ to be relatively low compared to the magnitude of the absolute peak current $i_{pc}$. The reagent layer 72 can be configured to generate a reduced mediator in a presence of an analyte, and the amount of the reduced mediator proximate to first electrode can contribute to the relatively high absolute peak current $i_{pc}$. In one embodiment at least the enzyme portion of the reagent layer 72 can be configured to not substantially diffuse from the first electrode to the second electrode when a sample is introduced into the test strip.

The test currents after $i_{pb}$ tends to settle to a flat region at approximately 1.3 seconds, and then the current increases again as the reduced mediator generated at the first electrode 166, which can be coated with the reagent layer 72, diffuses to the second electrode 164, which is not coated with the reagent layer 72. In one embodiment, a capacitance measurement can be performed at a relatively flat region of the test current values, which can be performed at about 1.3 seconds to about 1.4 seconds. Generally, if the capacitance is measured before 1 second, then the capacitance measurement can interfere with the relatively low first test potential $E_1$ that can be used to measure the first current transient $i_a(t)$. For example, an oscillating voltage component on the order of +/−50 mV superimposed onto a −20 mV constant voltage component can cause significant perturbation of the measured test current. Not only does the oscillating voltage component interfere with the first test potential $E_1$, but it can also significantly perturb the test currents measured at about 1.1 seconds, which in turn can interfere with blood glucose measurements including, for example, the determination of a correction factor for antioxidants. Following a great deal of testing and experimentation, it was finally determined that, surprisingly, measuring the capacitance at about 1.3 seconds to about 1.4 seconds resulted in accurate and precise measurements that did not interfere with the control solution/blood discrimination test or the blood glucose algorithm.

After the second test potential $E_2$, a third test potential $E_3$ (e.g., about +300 mV, as illustrated in FIG. 6) can be applied causing the test current to be measured at the first electrode 166, which can be coated with the reagent layer 72. The presence of a reagent layer on the first electrode can allow penetration of liquid between the spacer layer and the electrode layer, which can cause the electrode area to increase.

As illustrated in FIG. 6, in an exemplary embodiment a 109 Hz AC test voltage (±50 mV peak-to-peak) can be applied for 2 cycles during the time interval $t_{cap}$. The first cycle can be used as a conditioning pulse and the second cycle can be used to determine the capacitance. The capacitance estimate can be obtained by summing the test current over a portion of the alternating current (AC) wave, subtracting the direct current (DC) offset, and normalizing the result using the AC test voltage amplitude and the AC frequency. This calculation provides a measurement of the capacitance of the strip, which is dominated by the strip sample chamber when it is filled with a sample.

In one embodiment the capacitance can be measured by summing the test current over one quarter of the AC wave on either side of the point in time where the input AC voltage crosses the DC offset, i.e. when the AC component of the input voltage is zero (the zero crossing point). A derivation of how this translates to a measurement of the capacitance is described in further detail below. Equation 1 can show the test current magnitude as a function of time during the time interval $t_{cap}$:

$$i(t) = i_o + st + I \sin(\omega t + \phi) \qquad \text{Eq. 1}$$

where the terms $i_o + st$ represent the test current caused by the constant test voltage component. Generally, the DC current component is considered as changing linearly with time (due to the on-going glucose reaction generating ferrocyanide) and is thus represented by a constant $i_o$, which is the DC current at time zero (the zero crossing point), and s, the slope of the DC current change with time, t. The AC current component is represented by $I \sin(\omega t + \phi)$, where I is the amplitude of the current wave, $\omega$ is its frequency, and $\phi$ is its phase shift relative to the input voltage wave. The term $\omega$ can also be expressed as $2\pi f$, where f is the frequency of the AC wave in Hertz. The term I can also be expressed as shown in Equation 2:

$$I = \frac{V}{|Z|} \qquad \text{Eq. 2}$$

where V is the amplitude of the applied voltage signal and $|Z|$ is the magnitude of the complex impedance. The term $|Z|$ can also be expressed as shown in Equation 22:

$$|Z| = \frac{R}{\sqrt{1 + \tan^2 \phi}} = \frac{R}{\sqrt{1 + \omega^2 R^2 C^2}} \qquad \text{Eq. 3}$$

where R is the real part of the impedance and C is the capacitance.

Equation 1 can be integrated from one quarter wavelength before the zero crossing point to one quarter wavelength after the zero crossing point to yield Equation 4:

$$\int_{-1/4f}^{1/4f} i(t) = i_o [t]_{-1/4f}^{1/4f} + \frac{s}{2}[t^2]_{-1/4f}^{1/4f} + I \int_{-1/4f}^{1/4f} \sin(\omega t + \phi), \qquad \text{Eq. 4}$$

which can be simplified to Equation 5:

$$\int_{-1/4f}^{1/4f} i(t) = \frac{i_o}{2f} + \frac{I \sin \phi}{\pi f}. \qquad \text{Eq. 5}$$

By substituting Eq. 2 into Eq. 1, then into Eq. 4, and then rearranging, Equation 6 results:

$$C = \frac{1}{2V}\left(\int_{-1/4f}^{1/4f} i(t) - \frac{i_o}{2f}\right). \qquad \text{Eq. 6}$$

The integral term in Equation 6 can be approximated using a sum of currents shown in an Equation 7:

$$\int_{-1/4f}^{1/4f} i(t) \approx \frac{\frac{1}{n}\sum_{k=1}^{n} i_k}{2f} \qquad \text{Eq. 7}$$

where the test currents $i_k$ are summed from one quarter wavelength before the zero crossing point to one quarter wavelength past the zero crossing point. Substituting Equation 7 into Equation 6 yields Equation 8:

$$C = \frac{\frac{1}{n}\sum_{k=1}^{n} i_k - i_o}{4Vf}, \qquad \text{Eq. 8}$$

in which the DC offset current $i_o$ can be obtained by averaging the test current over one full sine cycle around the zero crossing point.

In another embodiment, the capacitance measurements can be obtained by summing the currents not around the voltage zero crossing point, but rather around the maximum AC component of the current. Thus, in Equation 7, rather than sum a quarter wavelength on either side of the voltage zero crossing point, the test current can be summed a quarter wavelength around the current maximum. This is tantamount to assuming that the circuit element responding to the AC excitation is a pure capacitor, so $\phi$ is $\pi/2$. Thus, Equation 5 can be reduced to Equation 9:

$$\int_{-1/4f}^{1/4f} i(t) = \frac{i_o}{2f} + \frac{I}{\pi f}. \qquad \text{Eq. 9}$$

This is believed to be a reasonable assumption in this case as the uncoated electrode is polarized such that the DC, or real, component of the current flowing is independent of the voltage applied over the range of voltages used in the AC excitation. Accordingly, the real part of the impedance responding to the AC excitation is infinite, implying a pure capacitive element. Equation 9 can then be used with Equation 6 to yield a simplified capacitance equation that does not require an integral approximation. The net result is that capacitance measurements when summing the currents not around the voltage crossing point, but rather around the maximum AC component of the current, were more precise.

CS/Blood Discrimination Test

In one embodiment, characteristics of control solution (CS) are used to distinguish control solutions from blood. For example, the presence and/or concentration of redox species in the sample, reaction kinetics, and/or capacitance can be used to distinguish control solutions from blood. The method disclosed herein can include the step of calculating a first reference value that is representative of the redox concentration in the sample and a second reference value that is representative of the rate of reaction of the sample with the reagent. In one embodiment, the first reference value is an interferent oxidation current and the second reference value is a reaction completion percentage. In some embodiments, a third reference value can be calculated by multiplying the first reference value by a capacitance index. The capacitance index can be any calculated value that is a capacitance or is related to, e.g., proportional to, a capacitance value. The capacitance index, for example, can be a measured capacitance, a known or predetermined capacitance, or any combination thereof. The capacitance index can also be related to any of the aforementioned capacitances and an empirically derived constant. In an exemplary embodiment, the capacitance index can be a ratio of a known capacitance to a measured capacitance or a ratio of a measured capacitance to a known capacitance. The known capacitance can be an average capacitance measured when blood samples are loaded into test strips of the same type as the test strip being used for the current test. The measured capacitance can be measured using the algorithm discussed above, for example.

In one embodiment, a CS/blood discrimination test can include a first reference value and a second reference value. The first value can be calculated based on the current values within the first time interval $T_1$ and the second reference value can be based on current values during both the second time interval $T_2$ and the third time interval $T_3$. In one embodiment the first reference value can be obtained by performing a summation of the current values obtained during the first time current transient when using the test voltage waveform of FIG. 6. By way of non-limiting example, a first reference value $i_{sum}$ can be represented by Equation 10:

$$i_{sum} = \sum_{t=0.05}^{1} i(t) \qquad \text{Eq. 10}$$

where the term $i_{sum}$ is the summation of current values and t is a time. As discussed above, in some embodiments, the first reference value can be multiplied by a capacitance index where the capacitance index can be a ratio of a known capacitance to a measured capacitance. In such embodiments, a third reference value $i_{capsum}$ can be represented by Equation 11:

$$i_{capsum} = \frac{C_{av}}{C_m} \sum_{t=0.05}^{1} i(t) \qquad \text{Eq. 11}$$

where $C_{av}$ is a known average capacitance, $C_m$ is a measured capacitance, and t is a time. In the exemplary embodiment of Equation 11, the ratio of $C_{av}$ to $C_m$ can be referred to as the capacitance index, which is discussed in more detail above. In one exemplary embodiment, the known average capacitance $C_{av}$ for an exemplary test strip according to an embodiment of the present invention is about 582 nanofarads.

The second reference value, sometimes referred to as the residual reaction index, can be obtained by a ratio Y of current values during the second time interval and the third time interval, as shown in Eq. 12:

$$Y = \text{abs}\left(\frac{i(3.8)}{i(4.15)}\right) \qquad \text{Eq. 12}$$

where abs represents an absolute value function and 3.8 and 4.15 represent the time in seconds of the second and third time intervals, respectively, for this particular example.

A discrimination criterion can be used to determine if the sample is either control solution or blood based on the first reference value of Eq. 10 or the third reference value of Eq. 11, and the second reference value of Eq. 12. For example, the first reference value of Eq. 10 or the third reference value of Eq. 11 can be compared to a pre-determined threshold and the second reference value of Eq. 12 can be compared to a pre-determined threshold function. The pre-determined threshold may be, for example, about 12 microamperes. The pre-determined threshold function can be based on a function using the first reference value of Eq. 10 or Eq. 11. More specifically, as illustrated by Eq. 13, where the calculated value of either of $i_{sum}$ or $i_{capsum}$ is represented by X, the pre-determined threshold function $F_{pdt}$ can be:

$$F_{PDT} = Z \frac{X - 12}{X} \qquad \text{Eq. 13}$$

where Z can be a constant such as, for example, about 0.2. Thus, the CS/Blood discrimination test can identify a sample as blood if $i_{sum}$ or $i_{capsum}$ is greater than or equal to the predetermined threshold, e.g., 12 microamperes, and if the ratio Y of current values during the second time interval and the third time interval, as shown in Eq. 12, is less than the value of the pre-determined threshold function $F_{pdt}$, else the sample is a control solution. In one embodiment, the CS/blood discrimination test can also be represented, for example, by Eq. 14:

$$\text{If } i_{capsum} \geq 12 \text{ and } Y < Z \frac{i_{capsum} - 12}{i_{capsum}}, \qquad \text{Eq. 14}$$

then sample is blood, else control solution

Figure 9:
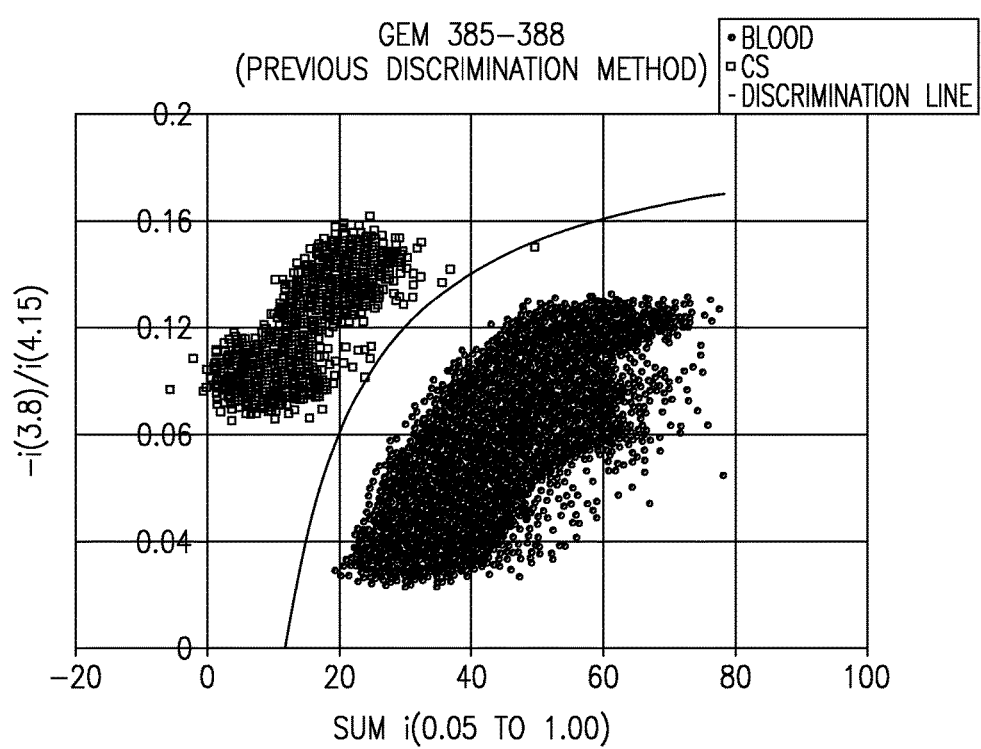
FIG. 9 is a chart showing a relationship between an interferent index and a residual reaction index for a plurality of blood samples (diamonds) and control solution samples (squares)

FIG. 9 is a chart showing a relationship between the first reference value $i_{sum}$ and the second reference value, sometimes referred to as the residual reaction index for a plurality of blood samples and control solution samples. By plotting the first reference value $i_{sum}$ on the X-axis and the second reference value, sometimes referred to as the residual reaction index, on the Y-axis, a segregation between blood and control solution can be observed. A discrimination line can be drawn to determine if the sample is either a control solution or blood. In FIG. 9, the first reference value $i_{sum}$ is a summation of the current values obtained during the first time current transient between about t=0.05 and about t=1 and the second reference value is $$\text{abs}\left(\frac{i(3.8)}{i(4.15)}\right).$$

By plotting the first reference value on the X-axis and the second reference value, sometimes referred to as the residual reaction index, on the Y-axis, a segregation between blood and control solution can be observed. It should be noted that the times (e.g., 3.8, 4.15) at which the current values were selected for the second reference value, sometimes referred to as the residual reaction index, were found empirically. A large number of current ratios were evaluated for their ability to discriminate between blood and control solution samples. The ratio used for the second reference value was selected because it was found to produce significant separation between blood and control solution samples.

Figure 10:
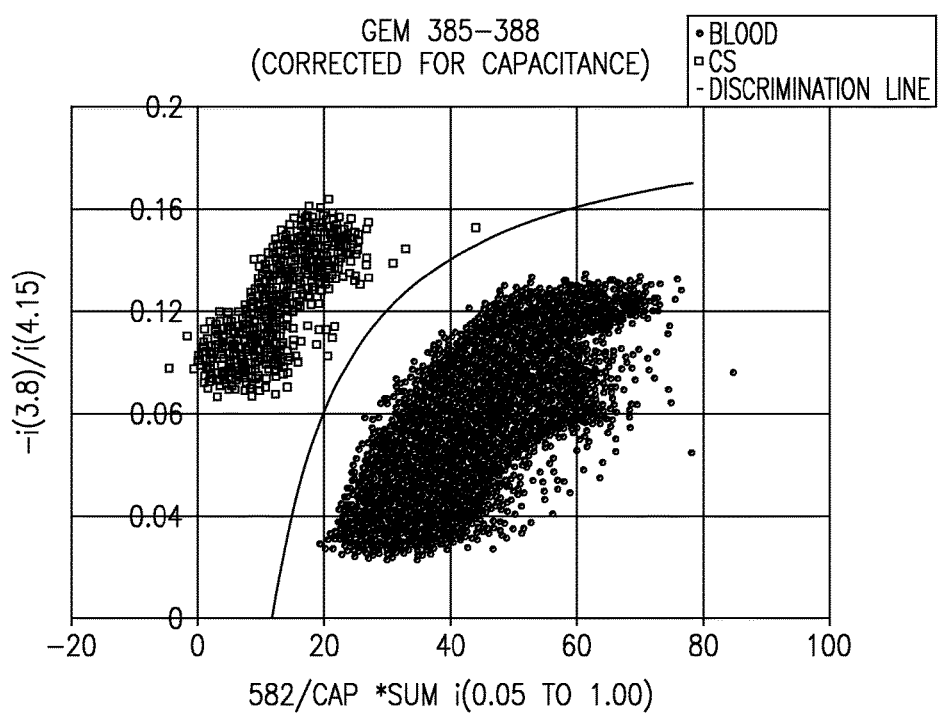
FIG. 10 is a chart showing, on the X-axis, an interferent index multiplied by a capacitance index and, on the Y-axis, a residual reaction index for a plurality of blood samples (diamonds) and control solution samples (squares).

FIG. 10 is a chart showing a relationship between the third reference value $i_{capsum}$ and the second reference value, sometimes referred to as the residual reaction index for a plurality of blood samples and control solution samples. In FIG. 10, the first reference value $i_{capsum}$ is a summation of the current values obtained during the first time current transient between about t=0.05 and about t=1 multiplied by a ratio of a known capacitance to a measured capacitance. As shown in FIG. 10, the modification of the first reference value by a capacitance index provides improved discrimination between control solution and blood samples.

In the method described herein, the information obtained from this statistical analysis of the first reference value $i_{sum}$ or the third reference value $i_{capsum}$ and the second reference value, sometimes referred to as the residual reaction index, can be used by the test meter to distinguish a control solutions from blood samples. The test meter can calculate the first reference value $i_{sum}$ or the third reference value $i_{capsum}$ and the second reference value and use these values in association with the derived discrimination line (or an equation representing the discrimination line) to distinguish control solutions from blood samples.

Blood Glucose Algorithm

Figure 8A:
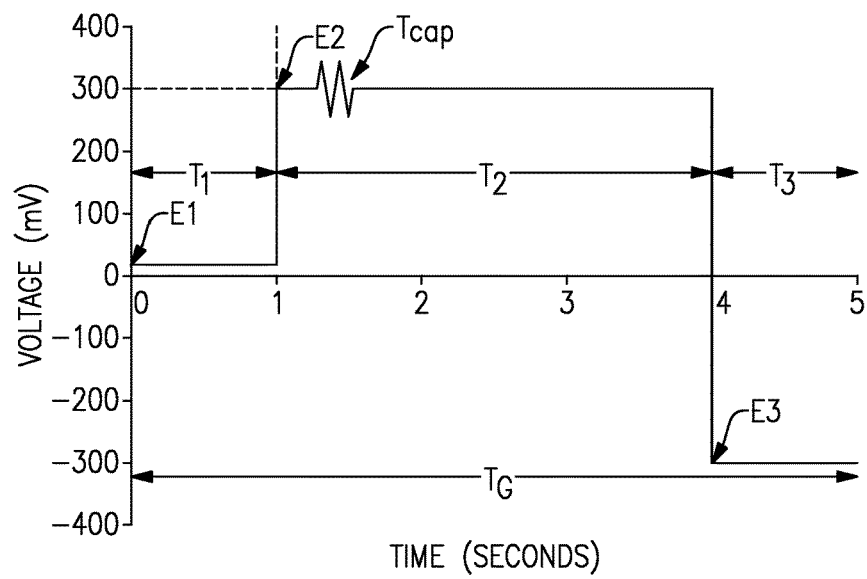
FIG. 8A illustrates a test voltage waveform in which the test meter applies a plurality of test voltages at opposite polarity for prescribed time intervals as compared to FIG. 6.

If the sample is identified as a blood sample, a blood glucose algorithm can be performed on the test current values. Assuming that a test strip has an opposing face or facing arrangement as shown in FIGS. 1A-4B, and that a potential waveform is applied to the test strip as shown in FIG. 6 or FIG. 8A, a glucose concentration [G] can be calculated using a glucose algorithm as shown in Equation (Eq.) 15:

$$[G] = \left(\frac{i_5}{i_6}\right)^p \times (a \times i_4 - Z) \qquad \text{Eq. 15}$$

In Eq. 15, [G] is the glucose concentration, $i_4$ is a first current value, $i_5$ is a second current value, and $i_6$ is a third current value, and the terms p, Z, and a are empirically derived calibration constants. A derivation of Eq. 15 can be found in a pending U.S. Published Patent Application No. 2007/0074977 (U.S. application Ser. No. 11/240,797), filed on Sep. 30, 2005 and entitled "Method and Apparatus for Rapid Electrochemical Analysis," the entirety of which is hereby incorporated herein by reference. All test current values (e.g., $i_4$, $i_5$, and $i_6$) in Equation 15 use the absolute value of the current. The first current value $i_4$ and the second current value $i_5$ are calculated from the third current transient and the third current value $i_6$ is calculated from the second current transient. Applicants note that the names "first," "second," and "third" are chosen for convenience and do not necessarily reflect the order in which the current values are calculated. In addition, all current values (e.g., $i_4$, $i_5$, and $i_6$) stated in Eq. 15 use the absolute value of the current.

In an embodiment, $i_5$ may be based on one or more current values collected during the third current transient and $i_6$ may be based on one or more current values collected during the second current transient. In another embodiment, $i_5$ may be based on one or more current values collected at about the end of the third current transient and $i_6$ may be based on one or more current values collected at about the beginning of the second current transient. Both $i_5$ and $i_6$ may be calculated using a summation, integration, or an average for a portion of the respective time intervals.

In another embodiment, the term $i_4$ can be defined to include peak current values from the second and third current transients to allow for more accurate glucose concentration as shown in Eq. 16:

$$i_4 = i_5 \left\{ \frac{i_{pc} - 2i_{pb} + i_{ss}}{i_{pc} + i_{ss}} \right\} \quad \text{Eq. 16}$$

The term $i_{pb}$ represents a peak current value for the second test potential time interval $T_2$ and the term $i_{pc}$ represents a peak current value for the third test potential time interval $T_3$. The term $i_{ss}$ is an estimate of the steady-state current, which is the current predicted to occur at long times after the application of the third test potential $E_3$ in the absence of on-going chemical reactions. Some examples of methods for calculating $i_{ss}$ can be found in U.S. Pat. Nos. 5,942,102 and 6,413,410, each of which is hereby incorporated by reference in its entirety. The use of peak current values to account for interferents in a physiological sample are described in U.S. Published Patent Application No. 2007/0227912 (U.S. patent application Ser. No. 11/278,341), filed on Mar. 31, 2006 and entitled "Methods and Apparatus for Analyzing a Sample in the Presence of Interferents," the entirety of which is hereby incorporated herein by reference.

In one embodiment, Eq. 15 and Eq. 16 can be used together to calculate a glucose concentration for either blood or a control solution. In another embodiment, the algorithm of Eq. 15 and Eq. 16 can be used for blood with a first set of calibration factors (i.e. a, p, and zgr) and a second set of calibration factors can be used for the control solution. When using two different sets of calibration factors, the methods described herein for discriminating between a test fluid and a control solution can improve the effectiveness of the analyte concentration calculations.

In addition, if the test meter determines that the sample is control solution (as opposed to blood), the test meter can store the resulting glucose concentration of the control sample such that a user can review test sample concentration data separately from control solution data. For example, the glucose concentrations for control solutions can be stored in a separate database, can be flagged, and/or discarded (i.e., not stored or stored for a short period of time).

Figure 8B:
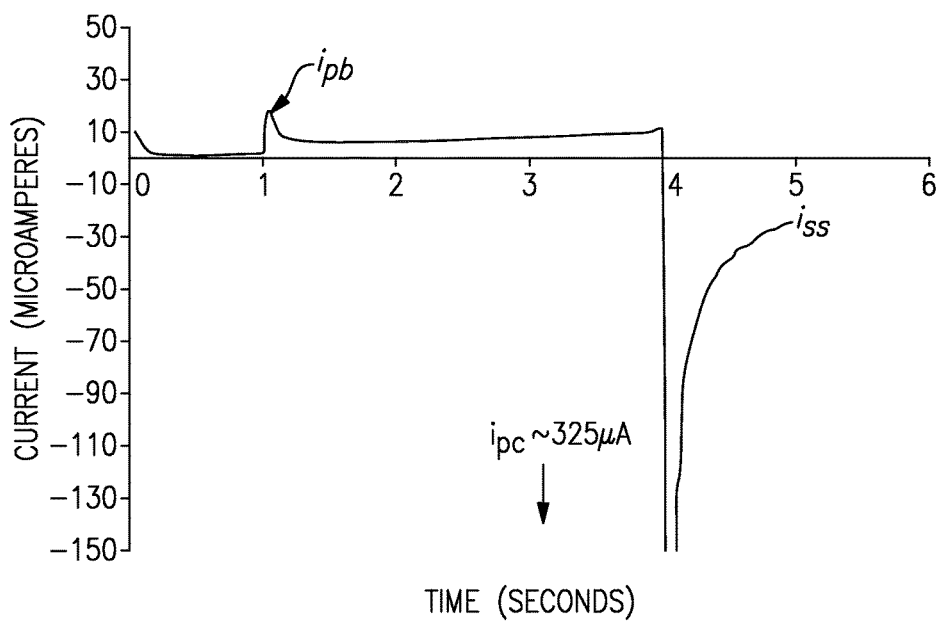
FIG. 8B illustrates a test current transient generated with the test voltages of FIG. 8A.

The example illustrated in FIGS. 6 and 7 shows the polarity of the first and second applied voltages as negative with a third applied voltage as positive when the electrode which is not coated with reagent acts as the reference electrode for the voltage measurement. However, the voltages applied can be of opposite polarity to the sequence illustrated in FIG. 6 if the electrode which is coated with reagent acts as the reference electrode for the voltage measurement. For example, in the preferred embodiment of FIGS. 8A and 8B, the polarity of the first and second applied voltages are positive with the polarity of the third applied voltage as negative. In both cases, the calculation of the glucose is the same because the electrode which is not coated with reagent acts as the anode during the first and second applied voltages, and the electrode which is coated with reagent acts as the anode during the third applied voltage.

Another advantage of being able to recognize a control solution is that a test meter can be programmed to automatically compare the results (e.g., glucose concentration) of the test of the control solution with the expected glucose concentration of the control solution. For example, the test meter can be pre-programmed with the expected glucose level(s) for the control solution(s). Alternatively, a user could input the expected glucose concentration for the control solution. When the test meter recognizes a control solution, the test meter can compare the measured control solution glucose concentration with the expected glucose concentration to determine if the meter is functioning properly. If the measured glucose concentration is out of the expected range, the test meter can output a warning message to alert the user.

One skilled in the art will appreciate further features and advantages of the presently disclosed system and method based on the above-described embodiments. Accordingly, the presently disclosed system and method are not to be limited by what has been particularly shown and described, except as indicated by the appended claims. All publications and references cited herein are expressly incorporated herein by reference in their entirety.

The invention claimed is:

1. A method for distinguishing between a blood sample and an aqueous non-blood sample using a test meter, the test meter having a processor, the method comprising the steps of:
   (a) using the test meter, applying a first test voltage for a first time interval, a second test voltage for a second time interval and a third test voltage for a third time interval for each of a plurality of aqueous non-blood samples applied to representative test strips, each test strip having an electrochemical cell;
   (b) using the test meter, calculating a first reference value and a second reference (Y) value for the plurality of aqueous non-blood samples, in which the first reference value is determined by a summation of current values measured by the test meter during the first time interval and the second reference value is determined by a ratio of current values obtained during the second and third time intervals;
   (c) using the test meter, calculating a third reference ($i_{capsum}$) value based on the first reference value, the third reference value being proportional to a capacitance index, the capacitance index ($C_{av}/C_m$) comprising a ratio of a pre-determined average capacitance of electrochemical cells measured when blood samples are loaded into test strips of the same type and an estimated capacitance of the electrochemical cell when the sample is introduced ($C_m$);
   (d) using the test meter, repeating steps (a)-(c) for a plurality of blood samples applied to representative test strips, each test strip having an electrochemical cell;
   (e) plotting the third reference value obtained from each of the aqueous non-blood samples and each of the blood samples on a first axis and plotting the second reference value obtained from each of the aqueous non-blood samples and each of the blood samples on a second axis and generating a discrimination line segregating the aqueous non-blood samples from the blood samples;
   (f) using the test meter, storing a discrimination relation based on the plotted discrimination line as a discrimination criteria;
   (g) applying an unknown sample to a test strip;
   (h) loading the sample into the test meter;
   (i) using the test meter, applying the first test voltage for the first time interval, the second test voltage for the second time interval and the third test voltage for the third time interval;

(j) measuring the capacitance of the unknown sample during the second time interval;
(k) determining the capacitance index of the unknown sample; and
(l) calculating the first reference value, the second reference value and the third reference value for the unknown sample and using the stored discrimination criteria to distinguish whether the unknown sample is a blood sample or an aqueous non-blood sample.

2. The method of claim 1, wherein the first reference value is representative of antioxidant concentration and the second reference value is representative of reaction kinetics.

3. The method of claim 1, wherein the plurality of aqueous non-blood samples comprise a plurality of control solutions.

4. The method of claim 1, wherein the discrimination criteria is applied as follows:
If $$i_{capsum} \geq 12 \text{ and } Y < Z \frac{icapsum - 12}{icapsum},$$

then sample is blood, else the applied sample is an aqueous non-blood sample, in which $Z$ is a constant of about 0.2.

5. The method of claim 1, in which the first, second and third test voltages are DC voltages and in which the capacitance of the electrochemical cell is estimated by applying an alternating AC wave during the second time interval with the second test voltage, and either summing the test current over one quarter of the alternating AC wave on either side of the zero crossing point or summing the test currents on either side of the maximum AC component of the current.

* * * * *